(12) United States Patent
Noh

(10) Patent No.: US 11,610,689 B2
(45) Date of Patent: Mar. 21, 2023

(54) METHOD FOR ADJUSTING TREATMENT BY USING ADJUSTED CONTINUOUS VARIABLES AND METHOD AND APPARATUS FOR ADJUSTING TREATMENT BY ANALYZING CORRELATIONS USING THE SAME

(71) Applicant: AJOU UNIVERSITY INDUSTRY—ACADEMIC COOPERATION FOUNDATION, Suwon-si (KR)

(72) Inventor: O Kyu Noh, Seoul (KR)

(73) Assignee: AJOU UNIVERSITY INDUSTRY—ACADEMIC COOPERATION FOUNDATION, Suwon-si (KR)

(*) Notice: Subject to any disclaimer, the term of this patent is extended or adjusted under 35 U.S.C. 154(b) by 823 days.

(21) Appl. No.: 16/269,639

(22) Filed: Feb. 7, 2019

(65) Prior Publication Data
US 2020/0075172 A1   Mar. 5, 2020

(30) Foreign Application Priority Data

Aug. 28, 2018 (KR) .................... 10-2018-0101420

(51) Int. Cl.
*G06N 20/00* (2019.01)
*G06N 7/00* (2023.01)
(Continued)

(52) U.S. Cl.
CPC ............. *G16H 50/70* (2018.01); *G06N 3/126* (2013.01); *G06N 7/00* (2013.01); *G06N 7/01* (2023.01); *G06N 20/00* (2019.01)

(58) Field of Classification Search
CPC ........ G16H 50/70; G16H 50/20; G16H 10/20; G06N 7/00; G06N 7/005; G06N 20/00; G06N 3/126; G05B 19/404
See application file for complete search history.

(56) References Cited

U.S. PATENT DOCUMENTS

| | | | |
|---|---|---|---|
| 2007/0203746 A1* | 8/2007 | DeHaan | G16H 40/63 600/300 |
| 2011/0076283 A1* | 3/2011 | Hegi | C12Q 1/6886 530/389.1 |

(Continued)

FOREIGN PATENT DOCUMENTS

| | | |
|---|---|---|
| JP | 2010142187 A * | 7/2010 |
| KR | 10-2013-0040014 A | 4/2013 |

(Continued)

OTHER PUBLICATIONS

"Normalization and Statistical Analysis of Quantitative Proteomics Data Generated by Metabolic Labeling" 2009, Ting et al., Molecular & Cellular Proteomics, vol. 8, Issue 10, p. 2227-2242, Oct. 1, 2009 (Year: 2009).*

*Primary Examiner* — Michael J Huntley
*Assistant Examiner* — Sehwan Kim
(74) *Attorney, Agent, or Firm* — Novick, Kim & Lee PLLC; Jae Youn Kim

(57) ABSTRACT

Provided are a method for adjusting a continuous variable, a method and an apparatus for analyzing a correlation using the same. A method for adjusting a continuous variable according to an exemplary embodiment of the present disclosure is a method for adjusting a continuous variable by an apparatus including: determining at least one confounder from analysis data; classifying the analysis data into a plurality of subgroups having the same combination of
(Continued)

confounders; and generating a new continuous variable for each subgroup based on a representative value of a continuous variable distribution.

6 Claims, 9 Drawing Sheets

(51) Int. Cl.
    *G16H 50/70*     (2018.01)
    *G06N 3/126*     (2023.01)
    *G06N 7/01*     (2023.01)

(56) References Cited

U.S. PATENT DOCUMENTS

2016/0063212 A1* 3/2016 Monier ................. G16H 10/60
    705/3
2021/0057110 A1* 2/2021 Han ....................... G16H 10/20

FOREIGN PATENT DOCUMENTS

| KR | 20130040014 A * | 4/2013 |
| KR | 10-2013-0098753 A | 9/2013 |
| KR | 10-2015-0116121 A | 10/2015 |
| KR | 10-2018-0041174 A | 4/2018 |
| WO | WO-2019005963 A1 * | 1/2019 |

* cited by examiner

METHOD FOR ADJUSTING TREATMENT BY USING ADJUSTED CONTINUOUS VARIABLES AND METHOD AND APPARATUS FOR ADJUSTING TREATMENT BY ANALYZING CORRELATIONS USING THE SAME

CROSS-REFERENCE TO RELATED APPLICATIONS

This application claims the priority to Korean Patent Application No. 10-2018-0101420 filed on Aug. 28, 2018, in the Korean Intellectual Property Office, the disclosure of which is incorporated herein by reference.

BACKGROUND

Field

The present disclosure relates to a method for adjusting treatment by using adjusted continuous variables and a method and an apparatus for adjusting treatment by analyzing correlations using the same, and more particularly, to a method for adjusting treatment by adjusting a continuous variable which adjusts continuous variables according to a confounder to generate a new continuous variable and a method and an apparatus for adjusting treatment by analyzing a correlation using the adjusted continuous variable and a specific dependent variable.

Description of the Related Art

In modern medical science, software with various statistical analysis algorithms is frequently used to find a cause of disease and a disease related factor and analyze the effect of newly developed drugs or treatments.

A liver function test level, a cholesterol level, a blood pressure, a body mass index (BMI), whether to smoke are clinic and epidemiologic variables which are representatively acquired in the hospital and variables acquired by measurement, observation, or experiment in accordance with the purpose of treatment or study may be expanded to dozens.

In the meantime, in some cases, the continuous variable (independent variable) may be correlated with a specific dependent variable. The continuous variable is represented by a number and a size of the number is significant. For example, the continuous variable may be an amount of drug administered to a patient and/or the number of drug administrations. The dependent variable is a variable (for example, a blood pressure of a patient) which is assumed to depend on the value of the continuous variable (independent variable). An actual relationship (for example, whether an amount of drugs received by the patient is related to the patient's blood pressure) between the continuous variable and the dependent variable may be determined using various statistical algorithms.

In the meantime, in some cases, the continuous variable is correlated with a specific dependent variable. For example, it is assumed that a person who consumes more coffee has a correlation with winning of more Nobel prizes. However, when the consumed coffee amount is directly correlated with a person's educational level or socioeconomic level, it is considered that rather than the consumed coffee amount (efficacy of the coffee), the high educational level and socioeconomic level are correlated with the Nobel prize winning. In this case, the consumed coffee amount is a "continuous variable", the Nobel prize winning is a "dependent variable", and the educational level or the socioeconomic level is a "confounder" therebetween. Therefore, when a result that there is a correlation between a certain continuous variable and the dependent variable is obtained, the influence of the confounder needs to be adjusted. Actually, when the confounder is adjusted, as illustrated in B of FIG. 1, it is reported that the consumed coffee amount and the winning of the Nobel prize are not affected.

Unlike the above case, even though it is considered that there is a correlation, as illustrated in C of FIG. 1, there is a case where a correlation is not seen. In this case, according to the current method, it is difficult to identify the correlation even though the confounder is adjusted in most cases.

However, even in C of FIG. 1, the correlation between the continuous variable and the dependent variable may be confounded in an unrelated direction, by the confounder. According to the method of adjusting a confounder of the related art, the confounder is adjusted while leaving the continuous variable as it is so that it is difficult to identify the correlation.

Therefore, there must be the correlation between the continuous variable and the dependent variable. However, there is a need to develop a technology for analyzing the correlation between the continuous variable and the dependent variable even when the correlation is not identified due to the confounder.

As a related art, there is Korean Unexamined Patent Application Publication No. 10-2015-0116121 (entitled a system and a method for predicting continuous dependent variable and a system and a method for predicting air cargo freight charge using the same, published on Oct. 15, 2015).

SUMMARY

An object to be achieved by the present disclosure is to provide a method for adjusting a continuous variable which is capable of analyzing a correlation between a continuous variable and a dependent variable even when there is a correlation between the continuous variable and a specific dependent variable but the correlation is not identified due to a confounder and a method and an apparatus for analyzing correlation using the same.

Technical problems of the present disclosure are not limited to the above-mentioned technical problem(s), and other technical problem(s), which is (are) not mentioned above, can be clearly understood by those skilled in the art from the following descriptions.

According to an aspect of the present disclosure, a method for adjusting a continuous variable is a method for adjusting a continuous variable by an apparatus including: determining at least one confounder from analysis data; classifying the analysis data into a plurality of subgroups having the same combination of confounders; and generating a new continuous variable for each subgroup based on a representative value of a continuous variable distribution.

Desirably, the determining may include: transforming clinical variables into categorical variables in the analysis data; calculating a significance probability (p-value) by comparing the clinical variable with the continuous variable; and determines a clinical variable having the significance probability which is smaller than a predetermined setting value as a confounder.

Desirably, the generating of a new continuous variable may include: setting a representative value of the continuous variable distribution for each subgroup to be "0"; and transforming the continuous variable of each subgroup into a relative value with respect to the set "0".

According to another aspect of the present disclosure, a method for analyzing a correlation using adjustment of a continuous variable is a method for analyzing a correlation between a continuous variable and a specific dependent variable for data to be analyzed by an apparatus, including: extracting information on a continuous variable, a dependent variable, and clinical variables from the data; determining at least one confounder from the clinical variables; transforming the continuous variable into a new continuous variable using the determined confounders; and analyzing a correlation between the new continuous variable and the dependent variable.

Desirably, the determining may include: transforming clinical variables into categorical variables in the analysis data; calculating a significance probability (p-value) by comparing the clinical variable with the continuous variable; and determines a clinical variable having a significance probability which is smaller than a predetermined setting value as a confounder.

Desirably, the transforming into a new continuous variable may include: classifying the data into a plurality of subgroups having the same combination of confounders; setting a representative value of the continuous variable distribution for each subgroup to be "0"; and transforming the continuous variable of each subgroup into a relative value with respect to the set "0".

According to another aspect of the present disclosure, a correlation analyzing apparatus using adjustment of a continuous variable, including: an adjusting unit which determines a confounder from data to be analyzed and transforms a continuous variable into a new continuous variable using the determined confounders; and a correlation analyzing unit which analyzes a correlation between the new continuous variable and a dependent variable.

Desirably, the adjusting unit may extract clinical variables from the data, calculate a significance probability (p-value) by comparing each clinical variable with a continuous variable; determine a clinical variable having a significance probability which is smaller than a predetermined setting value as a confounder; classify the data into a plurality of subgroups having the same combination of confounders; and transforms a continuous variable of each subgroup into a relative value with respect to "0" with "0" as a representative value of a continuous variable distribution for each subgroup to generate a new continuous variable.

According to the present disclosure, the continuous variable is adjusted by the confound so that even when there is a correlation between the continuous variable and a specific dependent variable, but the correlation is not identified due to the confound, the correlation between the continuous variable and the dependent variable may be analyzed.

The effects of the present disclosure are not limited to the technical effects mentioned above, and other effects which are not mentioned can be clearly understood by those skilled in the art from the following description

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
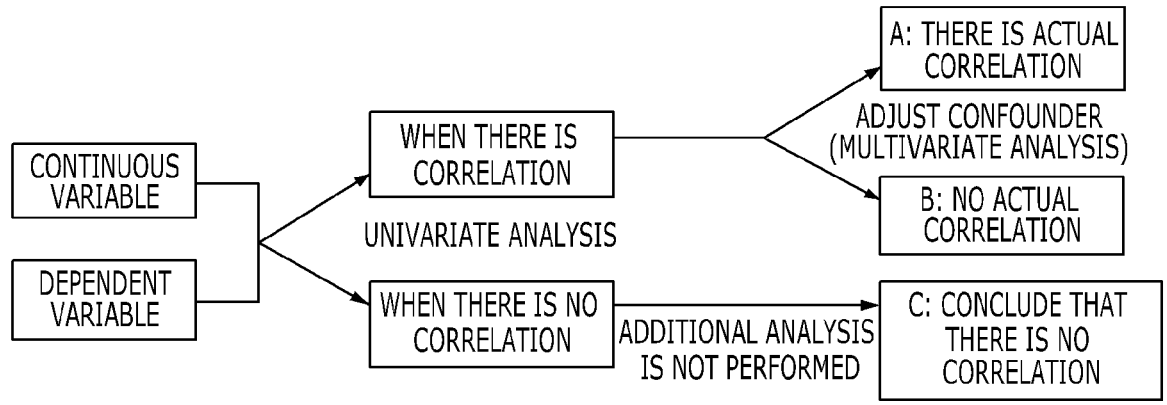
FIG. 1 is a view for explaining a process of identifying a general correlation.

Those skilled in the art may make various modifications to the present invention and the present invention may have various embodiments thereof, and thus specific embodiments will be illustrated in the drawings and described in detail in detailed description. However, this does not limit the present invention within specific exemplary embodiments, and it should be understood that the present invention covers all the modifications, equivalents and replacements within the spirit and technical scope of the present invention. In the description of respective drawings, similar reference numerals designate similar elements.

Terms such as first, second, A, or B may be used to describe various components but the components are not limited by the above terms. The above terms are used only to discriminate one component from the other component. For example, without departing from the scope of the present invention, a first component may be referred to as a second component, and similarly, a second component may be referred to as a first component. A term of and/or includes combination of a plurality of related elements or any one of the plurality of related elements.

It should be understood that, when it is described that an element is "coupled" or "connected" to another element, the element may be directly coupled or directly connected to the other element or coupled or connected to the other element through a third element. In contrast, when it is described that an element is "directly coupled" or "directly connected" to another element, it should be understood that no element is present therebetween.

Terms used in the present application are used only to describe a specific exemplary embodiment, but are not intended to limit the present invention. A singular form may include a plural form if there is no clearly opposite meaning in the context. In the present application, it should be understood that term "include" or "have" indicates that a feature, a number, a step, an operation, a component, a part or the combination those of described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

Hereinafter, exemplary embodiments according to the present invention will be described in detail with reference to accompanying drawings.

Figure 2:
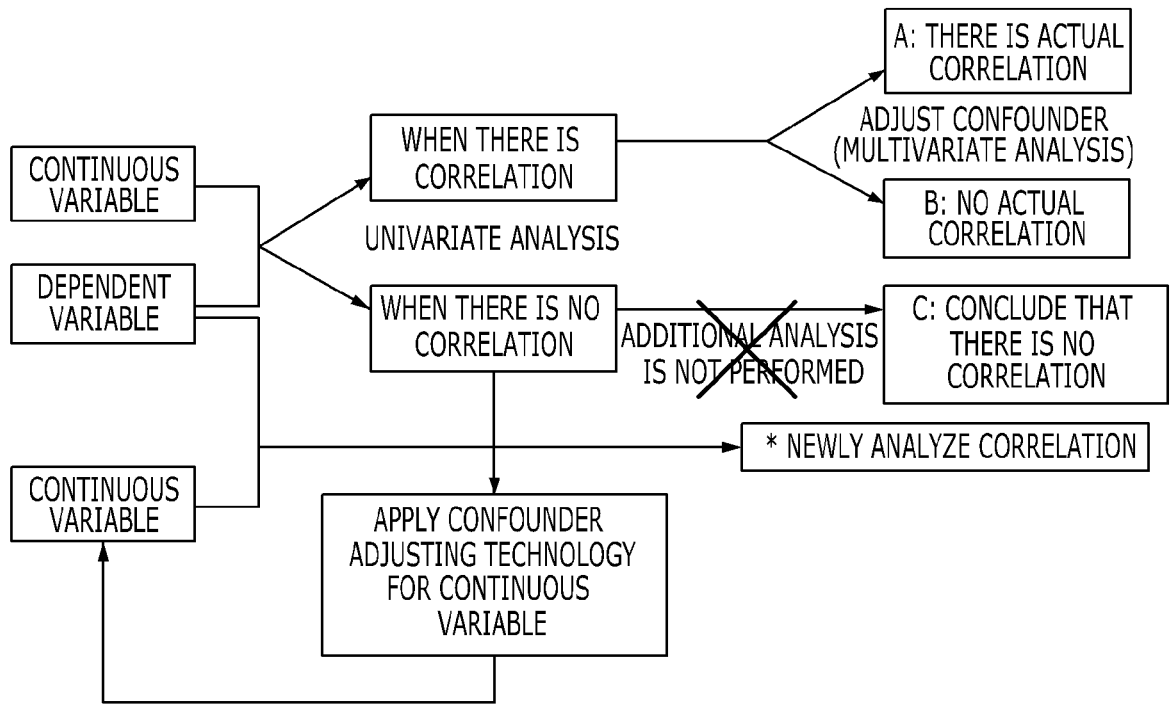
FIG. 2 is a view for explaining a process of identifying a correlation by applying a confounder adjusting technique according to an exemplary embodiment of the present disclosure.

FIG. 2 is a view for explaining a process of identifying a correlation by applying a confounder adjusting technique according to an exemplary embodiment of the present disclosure.

Referring to FIG. 2, a new continuous variable is generated by confirming and adjusting confounders for a continuous variable and a correlation between the new continuous variable and a dependent variable is analyzed. By doing this, when there is no correlation in an existing univariate analysis, the correlation may be newly analyzed after generating a new continuous variable by applying a confounder adjusting technique. By doing this, even though the continuous variable is correlated with a specific dependent variable but the correlation is not identified due to the confounder, the correlation between the continuous variable and the dependent variable may be analyzed.

Figure 3:
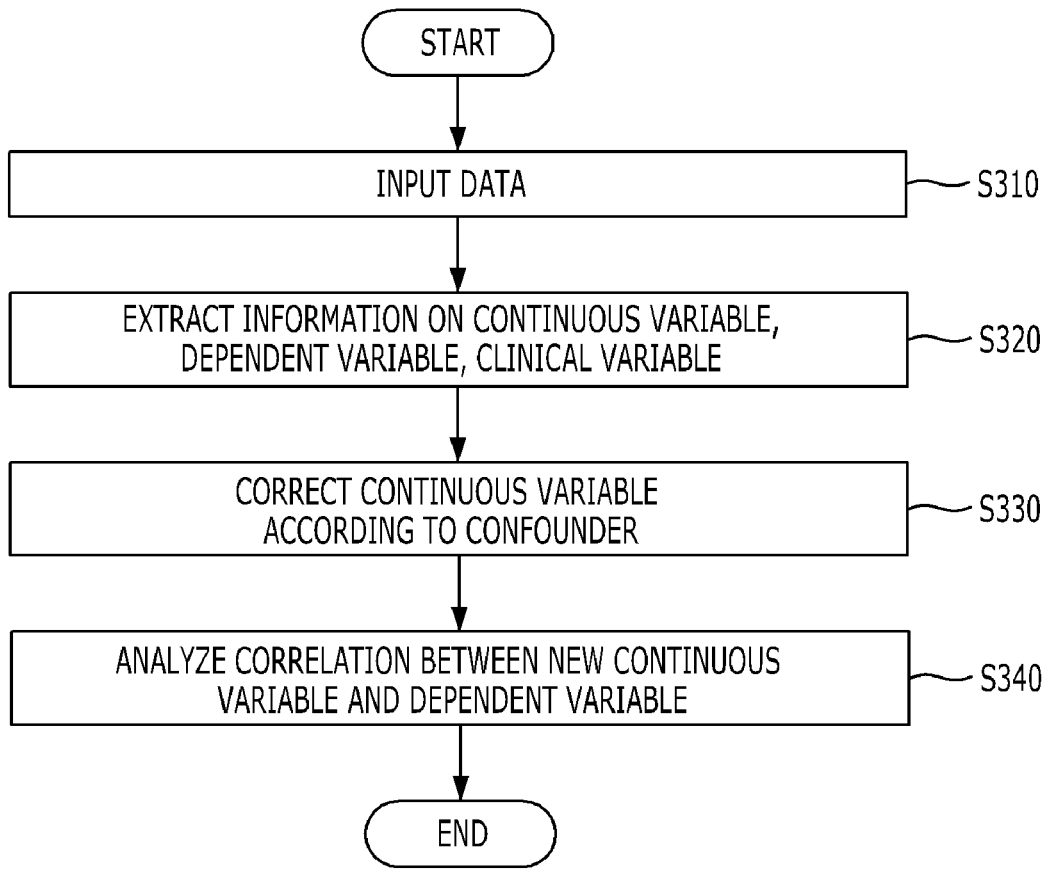
FIG. 3 is a flowchart for explaining a correlation analyzing method of a continuous variable according to an exemplary embodiment of the present disclosure.

FIG. 3 is a flowchart for explaining a correlation analyzing method of a continuous variable according to an exemplary embodiment of the present disclosure.

Referring to FIG. 3, when data to be analyzed is input in step S310, the apparatus extracts information on a continuous variable, a dependent variable, and clinical variables from the data in step S320. That is, when the data is input, the apparatus analyzes the data to obtain information on the continuous variable, the dependent variable, and other variables (hereinafter, referred to as clinical variables). In this case, the continuous variable and the dependent variable may be set in advance.

When step S320 is performed, the apparatus adjusts the continuous variable in accordance with a confounder to generate a new continuous variable in step S330 and analyzes a correlation between the new continuous variable and the dependent variable in step S340. That is, the apparatus determines confounders among clinical variables and transforms the continuous variable into a new continuous variable using the determined confounders. Thereafter, the apparatus analyzes a correlation between the new continuous variable and the dependent variable. In this case, the apparatus may analyze the correlation between the continuous variable and the dependent variable using various statistical algorithms such as a student's T test, Welch's T test, Kruskal-Wallis test, and Cox-proportional Hazard model.

A method for generating a new continuous variable using adjustment of a continuous variable according to a confounder by an apparatus will be described in more detail with reference to FIG. 4.

Figure 4:
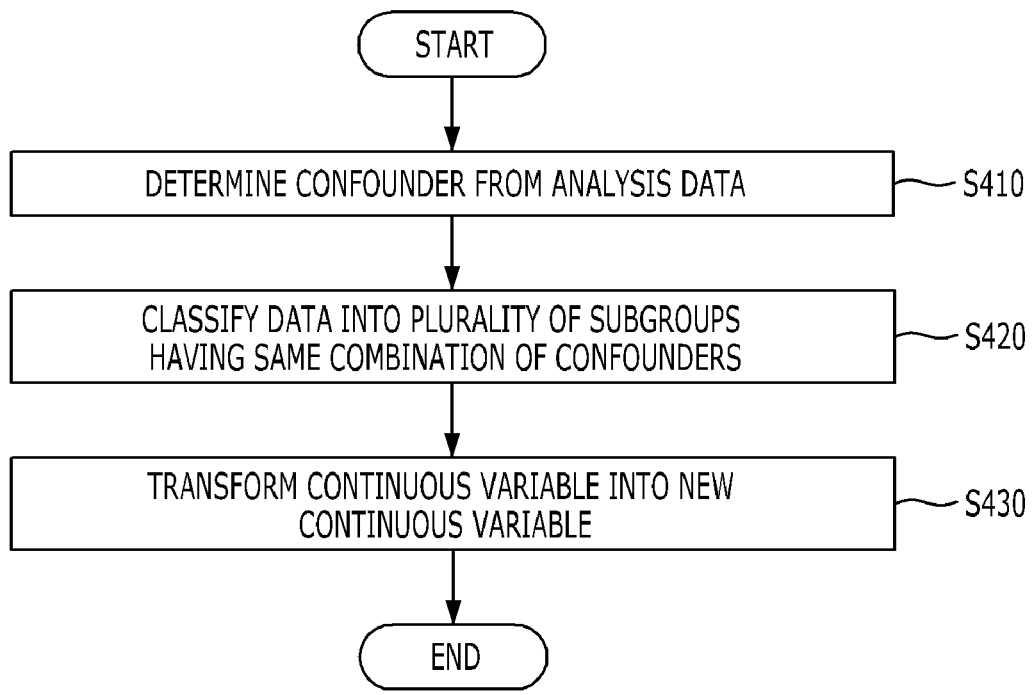
FIG. 4 is a flowchart for explaining an adjusting method of a continuous variable according to an exemplary embodiment of the present disclosure.
Figure 5:
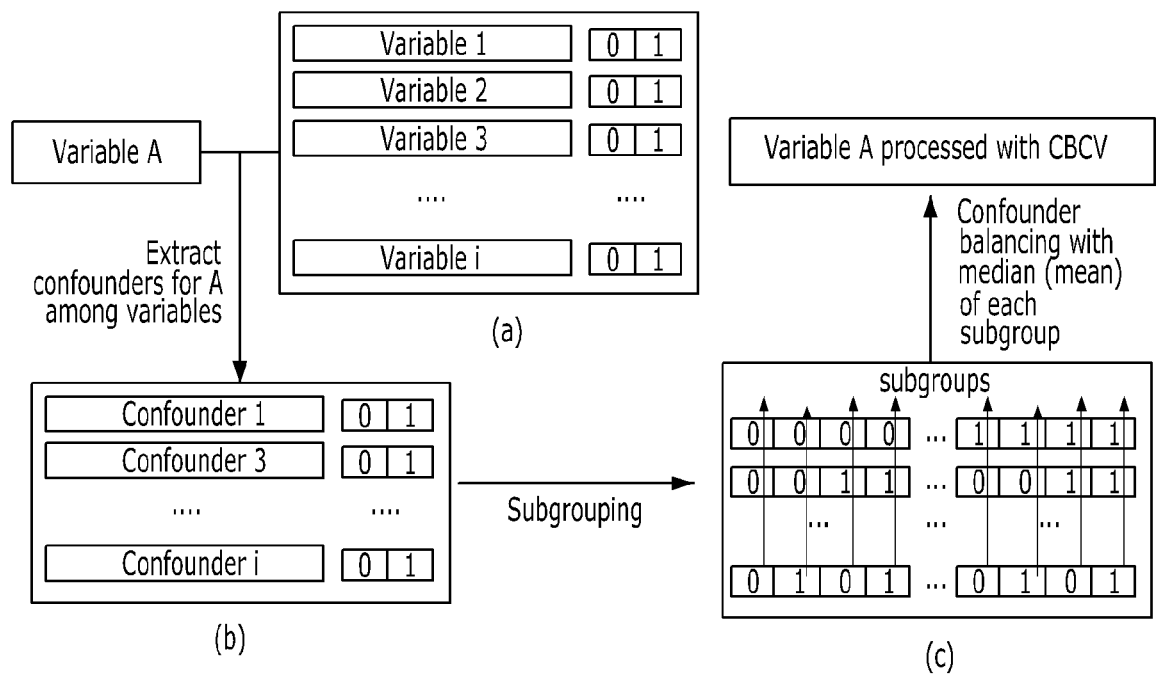
FIG. 5 is an exemplary view for explaining an adjusting method of a continuous variable according to an exemplary embodiment of the present disclosure.

FIG. 4 is a flowchart for explaining an adjusting method of a continuous variable according to an exemplary embodiment of the present disclosure and FIG. 5 is an exemplary view for explaining an adjusting method of a continuous variable according to an exemplary embodiment of the present disclosure;

Referring to FIG. 4, the apparatus determines at least one confounder from data to be analyzed in step S410. That is, the apparatus finds confounders which influence the continuous variable. A method for determining a confounder will be described in detail with reference to FIG. 6.

When step S410 is performed, the apparatus classifies data to be analyzed into a plurality of subgroups having the same combination of confounders in step S420.

For example, as illustrated in FIG. 5A, when clinical variables 1, 2, . . . i are given, the apparatus extracts confounders 1, 3, . . . i from the clinical variables as illustrated in FIG. 5B. Thereafter, the apparatus classifies a plurality of subgroups having the same combination of confounders as illustrated in FIG. 5C. In this case, it is assumed that a value of a first confounder confounder 1 is configured by 1 and 0, a value of a second confounder confounder 3 is configured by 1 and 0, and a value of an i-th confounder confounder i is configured by 1 and 0. In this case, combinations of first to i-th confounders are (0, 0, . . . , 0), (0, 0, . . . , 1), . . . , (1, 1, . . . , 0), and (1, 1, . . . , 1) so that the apparatus generates a plurality of subgroups having the same combination of the first to i-th confounders as illustrated in FIG. 5C. That is, the apparatus generates subgroups such that data having a combination (0, 0, . . . , 0) in which values of first to i-th confounders are 0 is a first subgroup, data having a combination (0, 0, . . . , 1) in which values of first to i−1-th confounders are "0" and a value of the i-th confounder is "1" is a second subgroup, and data having a combination (0, 0, . . . , 1, 1) in which values of first to i−2-th confounders are "0" and values of the i−1-th and i-th confounders are "1" is a third subgroup.

When step S420 is performed, the apparatus adjusts the continuous variable of each subgroup according to a confounder to generate a new continuous variable in step S430. That is, the apparatus sets a representative value of continuous variable distribution for every subgroup to be "0" to generate a new continuous variable. A method for generating a new continuous variable will be described in more detail with reference to FIG. 8.

Figure 6:
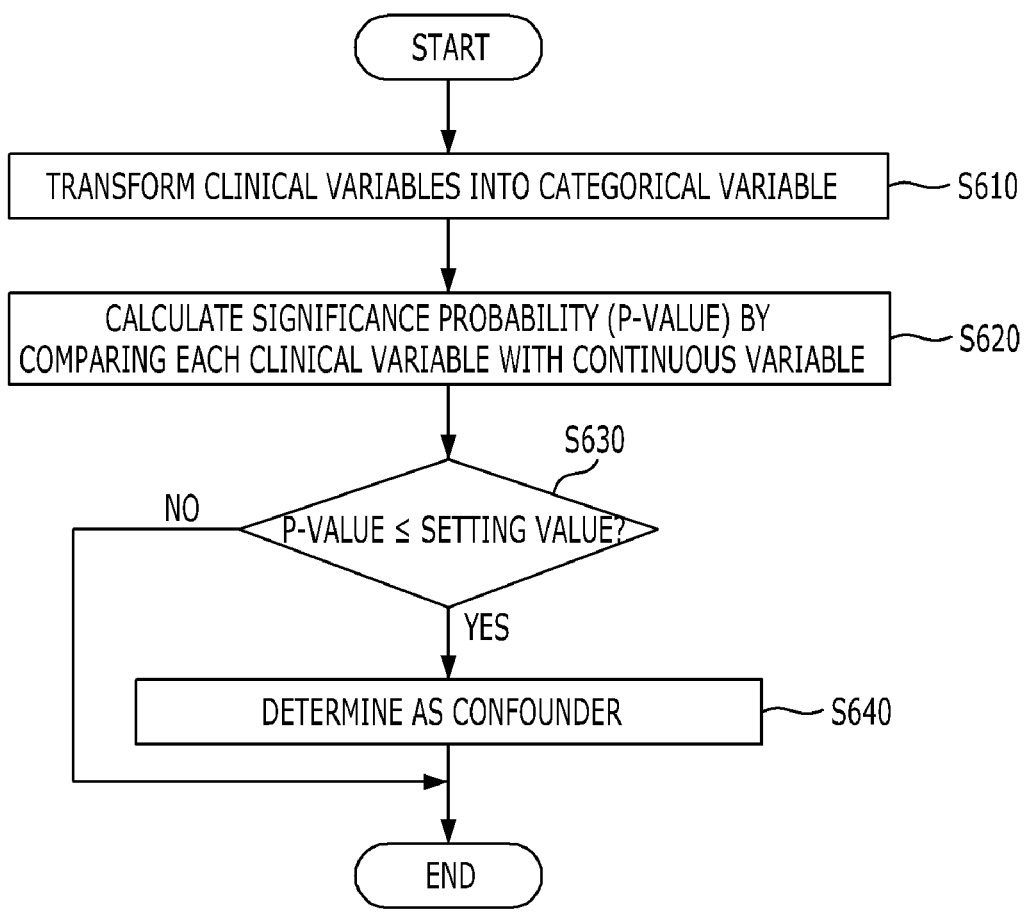
FIG. 6 is a flowchart for explaining a method for determining a confounder according to an exemplary embodiment of the present disclosure.
Figure 7:
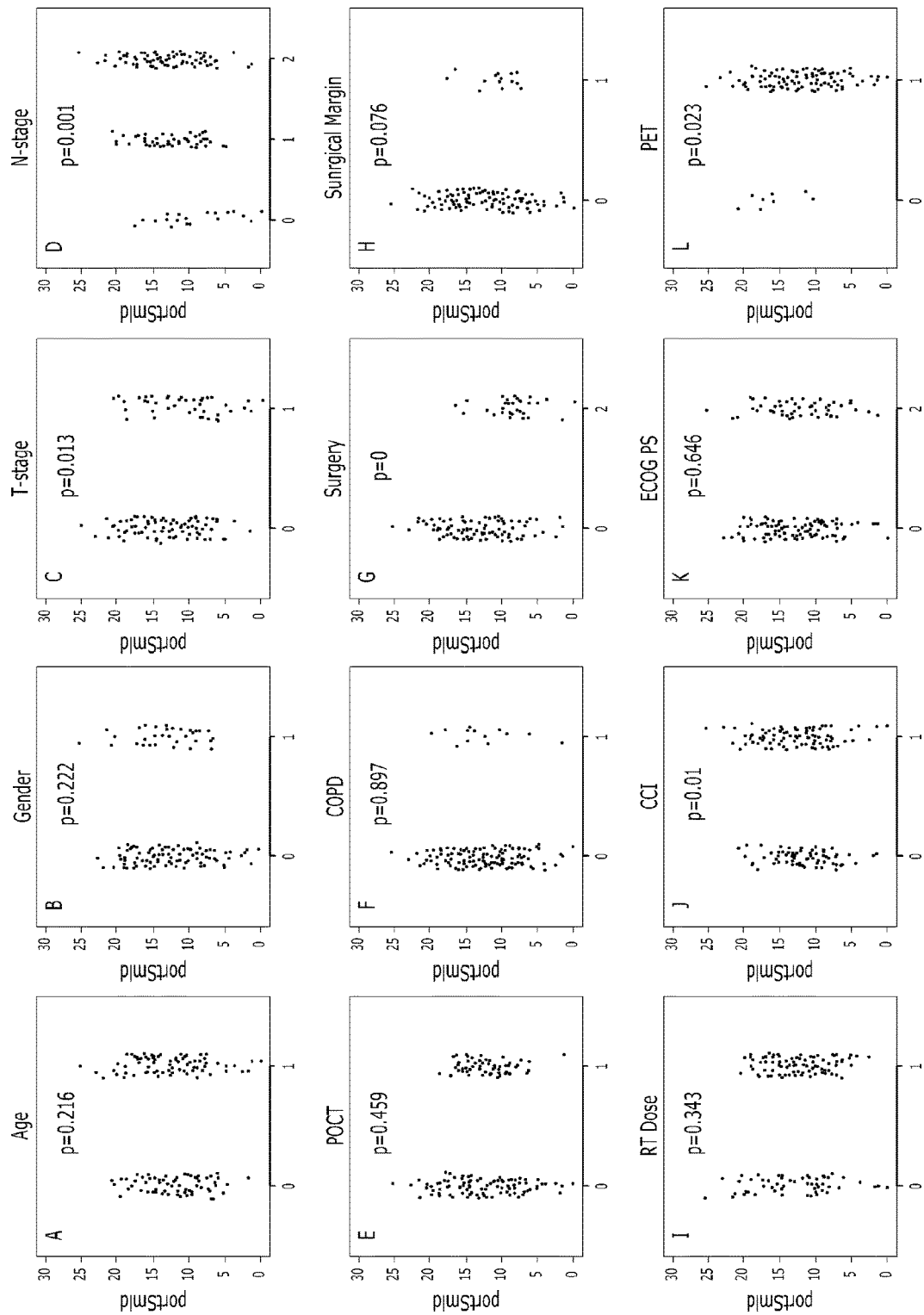
FIG. 7 is a scatter diagram for confirming a confounder which influences a continuous variable according to an exemplary embodiment of the present disclosure.

FIG. 6 is a flowchart for explaining a method for determining a confounder according to an exemplary embodiment of the present disclosure and FIG. 7 is a scatter diagram for confirming a confounder which influences a continuous variable according to an exemplary embodiment of the present disclosure.

Referring to FIG. 6, the apparatus transforms clinical variables into a categorical variable in the analysis data in step S610. The clinical variable extracted from the analysis data includes a continuous variable and a categorical variable. That is, the clinical variable includes a categorical variable such as sex and a continuous variable such as age. Therefore, the apparatus divides the continuous variable by a specific value (for example, a median) to be transformed into a categorical variable.

When step S610 is performed, the apparatus calculates a significance probability (p-value) by comparing each clinical value with the continuous variable in step S620.

Thereafter, the apparatus compares the significance probability with a predetermined setting value in step S630 to determine a clinical value in which the significance probability is smaller than the setting value as a confounder in step S640. That is, the apparatus compares each clinical variable with an average of the continuous variable to identify whether the difference is statistically significant. As a result, only clinical variables whose p-value is smaller than a setting value (for example, 0.1) are determined as confounders which influence the continuous variable.

When the method for determining confounder is described with reference to FIG. 7, in the scatter diagram, a horizontal axis represents a value of each clinical variable (potential confounder) and a vertical axis represents a mean lung dose (MLD) which is a continuous variable. In this case, the value of each clinical variable is not a continuous variable, but a categorical variable. Therefore, the scatter diagrams schematically show whether the MLD varies depending on each clinical variable. In FIG. 7, it is visually confirmed that the MLD varies depending on variables as illustrated in C, D, and G. However, the difference is not visually verified, but the average of the MLD is compared for every variable to confirm whether the difference is statistically significant. As a result, only the clinical values whose p-value is smaller than 0.1 are considered as confounders which influence the MLD.

In the meantime, even though a level of p-value is determined to be 0.1, the level of p-value may vary depending on a situation.

Figure 8:
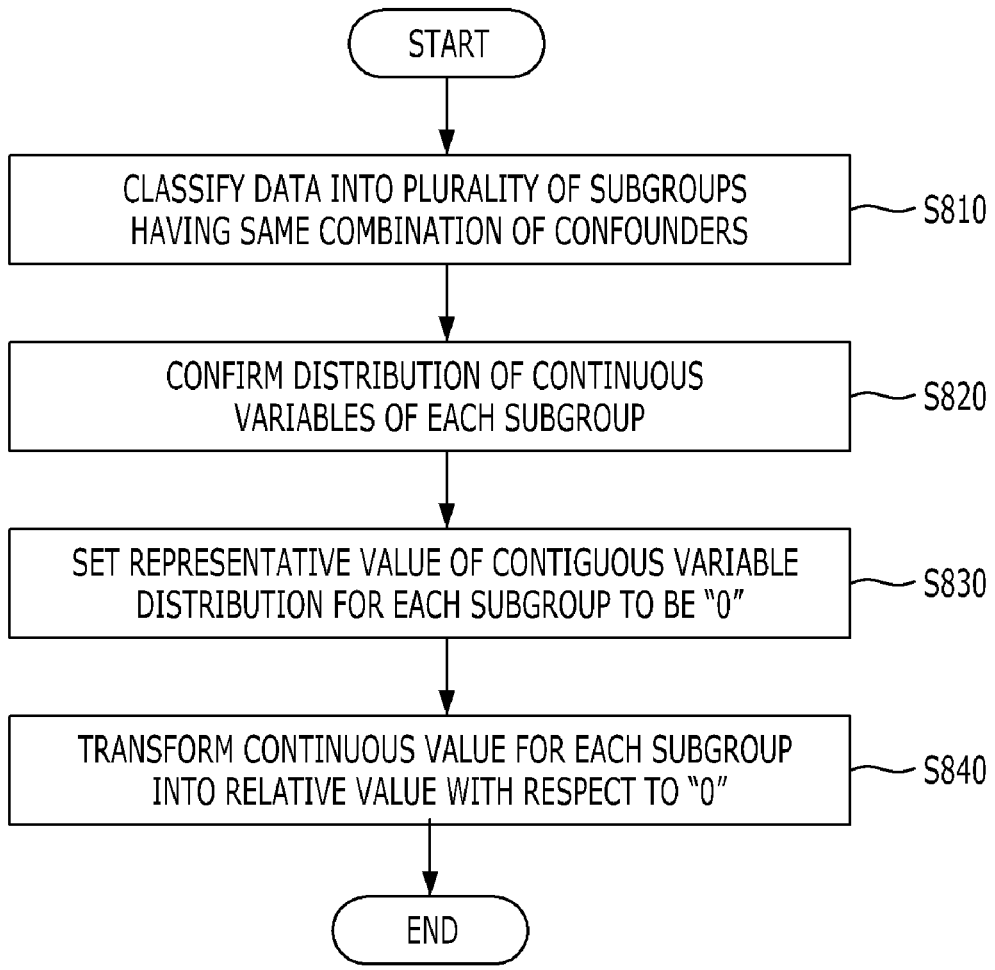
FIG. 8 is a flowchart for explaining a method for generating a new continuous variable according to an exemplary embodiment of the present disclosure.
Figure 9:
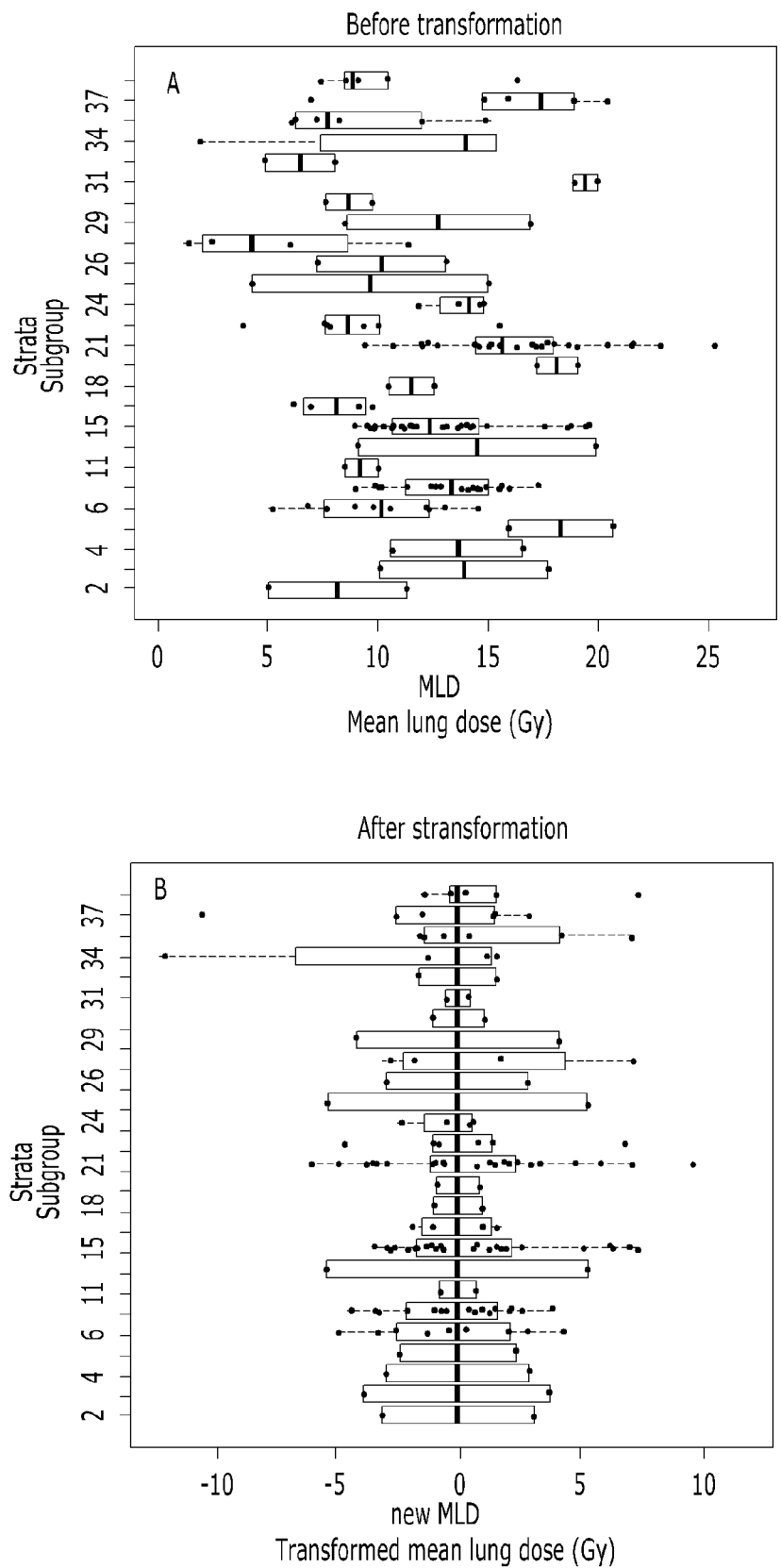
FIG. 9 is an exemplary view for explaining a process of adjusting an influence of a confounder with a median for every subgroup which shares confounders for a continuous variable according to an exemplary embodiment of the present disclosure.
Figure 10:
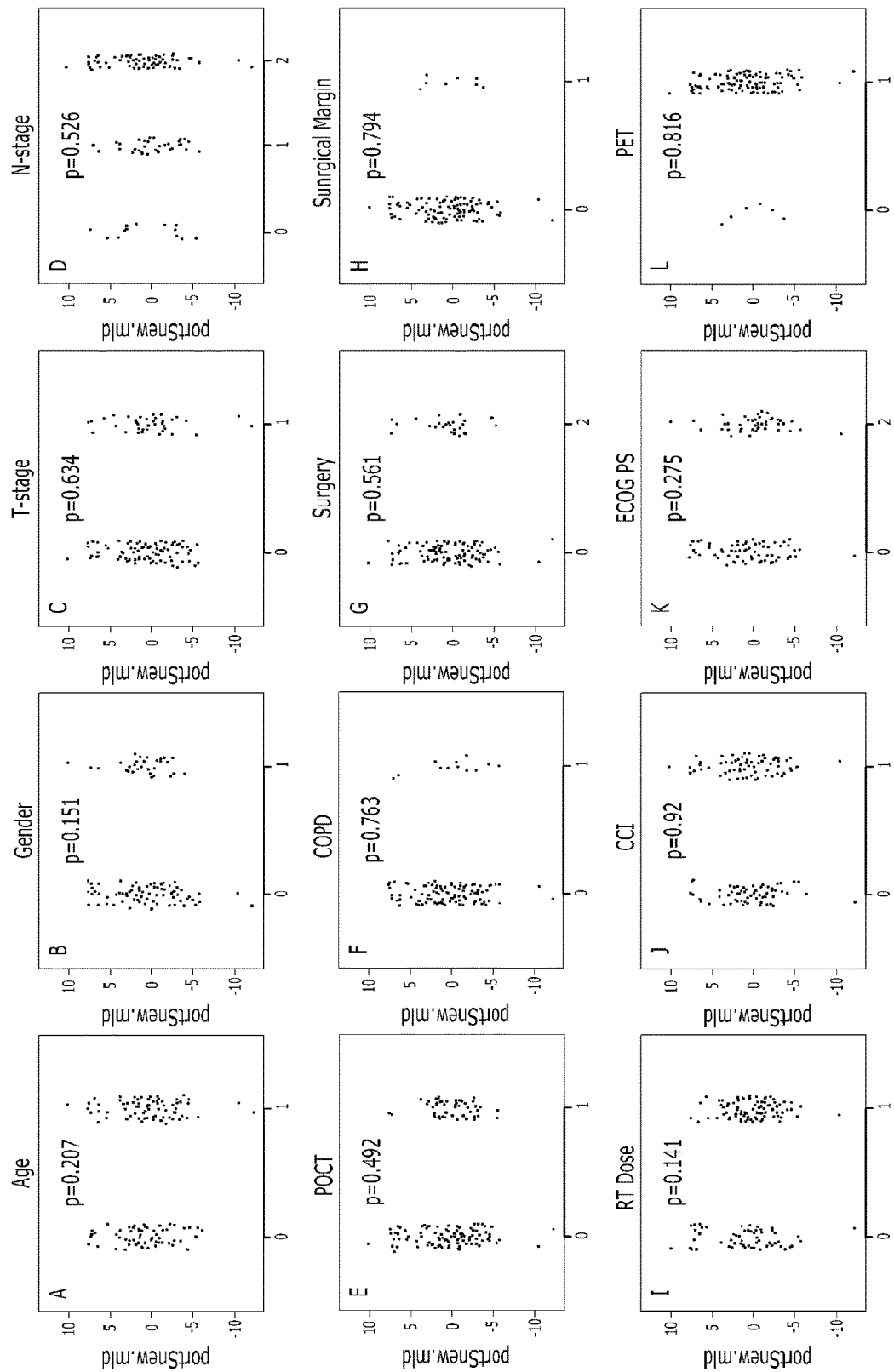
FIG. 10 is an exemplary view for confirming that a confounder is adjusted for an adjusted continuous variable according to an exemplary embodiment of the present disclosure.

FIG. 8 is a flowchart for explaining a method for generating a new continuous variable according to an exemplary embodiment of the present disclosure, FIG. 9 is an exemplary view for explaining a process of adjusting an influence of a confounder with a median for every subgroup which shares confounders for a continuous variable according to an exemplary embodiment of the present disclosure, and FIG. 10 is an exemplary view for confirming that a confounder is adjusted for an adjusted continuous variable according to an exemplary embodiment of the present disclosure.

Referring to FIG. 8, the apparatus classifies data to be analyzed into a plurality of subgroups having the same combination of confounders in step S810.

Thereafter, the apparatus confirms the distribution of the corresponding continuous variable of each subgroup in step S820, sets a representative value of continuous variable distribution for every subgroup to be "0" in step S830, and transforms the continuous variable of each subgroup into a relative value with respect to the set "0" in step S840. By doing this, the continuous variable is transformed into a new continuous variable which is adjusted according to a confounder. Here, even though the representative value may include a median and a mean value, in the following description, the representative value is limited to a median. In this case, the apparatus assumes the median of the continuous variable distribution for every subgroup as "0" and transforms the value of the continuous variable of each subgroup into a relative value with respect to "0".

For example, a method for generating a new continuous variable when the continuous variable of the first subgroup is configured by 4, 6, 7, 8, 11, 15, 17, 18, and 19 will be described. Since a median of the first subgroup is "11", "11" is transformed into "0". By doing this, the continuous variables {4, 6, 7, 8, 11, 15, 17, 18, 19} may be transformed into relative values {−7, −5, −4, −3, 0, 4, 6, 7, 8} with respect to "0". In this case, the transformed {−7, −5, −4, −3, 0, 4, 6, 7, 8} may be new continuous variables.

Further, an example that combinations of variables are created and C, D, G, H, J, L determined as confounders in FIG. 7 are divided into subgroups having a value of each combination will be described. In this case, theoretically, 96 (C(2)×D(3)×G(2)×H(2)×J(2)×L (2)) subgroups are generated. However, in each subgroup, when there is no person corresponding to a subgroup or one person corresponds to a subgroup, the subgroups are excluded and subgroups having two or more persons are included. Therefore, as illustrated in FIG. 9, new continuous variables new MLD are generated using 38 subgroups. Here, even though two or more persons are used, how many person or data is included in each subgroup may vary depending on the user's setting.

Referring to FIG. 9, when MLDs are transformed into new relative MLDs, for every subgroup in A with "0" as a representative value of the MLD, B may be obtained.

A scatter diagram of how the new MLDs transformed as described above are distributed again according to the clinical variable is illustrated in FIG. 10. This may be a process for confirming whether variables which confound the corresponding continuous variables still confound the adjusted new continuous variables or are satisfactorily adjusted. Regardless of whether variables are used for transformation or not, it is understood that there is no factor which confounds the new MLDs when averages are compared.

It is confirmed that the corresponding continuous variable is correlated with a dependent variable that we actually want to know by a technology of confirming and adjusting confounders for the new continuous variables to generate new continuous variables.

Figure 11:
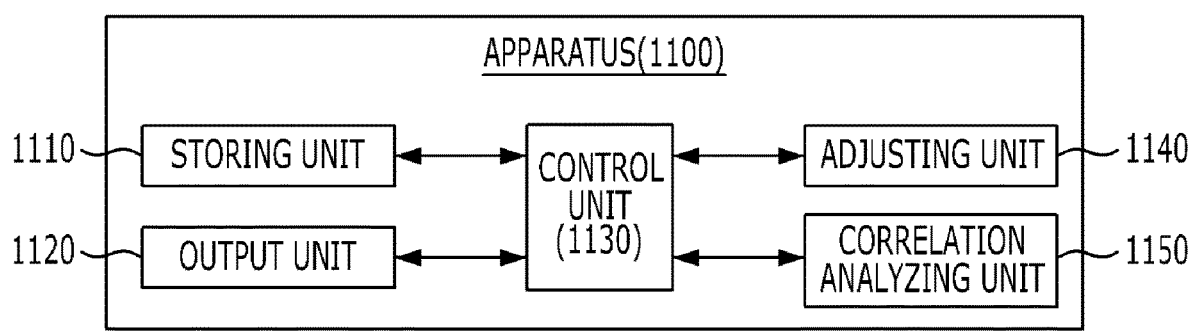
FIG. 11 is a view for explaining an apparatus for analyzing a correlation using the adjustment of a continuous variable according to an exemplary embodiment of the present disclosure.

FIG. 11 is a view for explaining an apparatus for analyzing a correlation using the adjustment of a continuous variable according to an exemplary embodiment of the present disclosure.

Referring to FIG. 11, an apparatus for analyzing correlation using adjustment of a continuous variable according to an exemplary embodiment of the present disclosure includes a storing unit 1110, an output unit 1120, a control unit 1130, an adjusting unit 1140, and a correlation analyzing unit 1150.

The storing unit 1110 is a configuration of storing data related to an operation of an apparatus 1100 for analyzing a correlation using adjustment of the continuous variable. Here, as the storing unit 1110, known storage media may be used and for example, any one or more of known storage media such as ROM, PROM, EPROM, EEPROM, and RAM may be used.

Specifically, in the storing unit 1110, a technology of adjusting a continuous variable according to a confounder and a program or an application for analyzing a correlation may be stored. Further, in the storing unit 1110, a technology of adjusting a continuous variable according to a confounder and various related algorithms (or mathematical equations) for analyzing a correlation may be stored. In this case, the control unit 1130 calls the storing unit 1110 to obtain a necessary algorithm.

The output unit 1120 is a configuration for displaying various information related to an operation of an apparatus 1100 for analyzing a correlation of the continuous variable using adjustment of the continuous variable. Specifically, the output unit 1120 may display various information such as continuous variables adjusted according to the confounder in the adjusting unit 1140 and a correlation between the continuous variable and the dependent variable analyzed by the correlation analyzing unit 1150. Such an output unit 1120 may be implemented by various display devices including an LCD and an LED.

The control unit 1130 is a configuration of controlling operations of various components of an apparatus 1100 for analyzing a correlation of continuous variables using adjustment of the continuous variable and includes at least one arithmetic device. Here, the arithmetic device may be a general purpose central operation unit (CPU), a programmable device element (CPLD or FPGA) implemented to be suitable for a specific purpose, and an application specific integrated circuit (ASIC) or a microcontroller chip.

The adjusting unit 1140 determines a confounder from data to be analyzed and transforms the continuous variable into a new continuous variable using the determined confounder. That is, the adjusting unit 1140 extracts a clinical variable from the data, calculates a significance probability (p-value) by comparing the continuous variable with each clinical variable, and determines a clinical variable whose significance probability is lower than a predetermined setting value as a confounder. Thereafter, the adjusting unit 1140 classifies the data into a plurality of subgroups having the same combination of confounders and transforms a continuous variable of each subgroup into a relative value with respect to "9" with "0" as a representative value of the continuous variable distribution for every subgroup. By doing this, the continuous variable is transformed into a new continuous variable.

The correlation analyzing unit 1150 analyzes a correlation between the new continuous variable generated in the adjusting unit 1140 and the dependent variable. In this case, the correlation analyzing unit 1150 analyzes the correlation using Cox-proportional Hazard Model.

According to an exemplary embodiment of the present disclosure, the adjusting unit 1140 and the correlation analyzing unit 1150 may be program modules which communicate with an external terminal device or an external server. Such program modules are an operating system, an application program module, and other program modules and included in the apparatus 1100 and physically stored in various known storage devices. Further, the program modules may be stored in a remote storage device which is capable of communicating with the apparatus 1100. The program modules comprehensively include a routine, a subroutine, a program, an object, a component, or a data structure which performs the above-described specific task according to the present disclosure or executes a specific abstract data type, but the present invention is not limited thereto.

In the meantime, the apparatus 1100 may be a communication terminal such as a computer, a notebook, a net book, or a PDA or may be a smart device such as a smart phone, a smart note, a tablet PC, or a smart TV. Further, the apparatus 1100 may be implemented by a single arithmetic device or implemented as an aggregation device in which two or more arithmetic devices are connected. For example, the apparatus 1100 may be implemented by a single server or implemented such that two or more servers are connected.

Hereinafter, the present disclosure will be described with a radiation therapy and a survival rate of lung cancer patients as an example.

A goal of a radiation therapy of the lung cancer is to lower recurrence rates by destroying cancer cells and consequently improve the survival rate. However, the radiation therapy has toxicity which damages normal tissues and side effects which are caused by the toxicity adversely influence the health of the patient so that the radiation therapy may lower the survival rate. Therefore, it is very important to minimize potential adverse effects by minimizing a radiation dose of the normal tissues during the radiation therapy.

In the meantime, an organ which causes a representative side effect in the radiation therapy of the lung cancer is the lung itself. The radiation therapy treats tumors in the lung so that it is difficult to completely avoid the radiation exposure of the lung. Therefore, many people suggest a dose limit of the radiation exposure which minimizes a probability of side effects and it is known that there is no side effect and there is no negative effect on the survival rate below the dose limit.

For example, when 178 lung cancer patients who are treated with radiation therapy after lung cancer surgery are analyzed, it shows that the exposure amount of the lung at the time of radiation therapy does not negatively influence the survival rate. The mean lung dose (MLD) used here is an average value of an exposure amount of the lung of the patient at the time of radiation therapy and is frequently used to indicate the lung exposure amount of the patient.

A result of the Cox-proportional hazard model for the survival rate of the MLD of the related is as follows:

Hazard Ratio: 0.99

Confidence interval (95% confidence interval of hazard ratio): 0.94-1.04

P-value (probability): 0.651

Here, the "hazard ratio" indicates a relative hazard ratio to the survival rate when the exposure dose (MLD) of the lung increases by a unit value (1 Gy). When the hazard ratio is 1, it means that even though the exposure dose increases, the hazard ratio does not increase nor decrease. When the hazard ratio is 0.99, it means that as the exposure dose (MLD) of the lung increases by 1 Gy, the survival rate decreases. However, since the 95% confidence interval of the hazard ratio includes 1, it is hard to say that the increase or decrease of the MLD does not influence the survival rate. That is, it is not known whether the lung exposure dose adversely influences the survival rate from the result.

However, this is because factors (for example, sex, age, a stage of lung cancer, a range of surgery, completeness of surgery, underlying lung disease, and comorbidity) which may influence the survival rate of the patient confound the MLD value to dilute significant results. In order to adjust the confounder, the confounder is included in the Cox-proportional Hazard Model to perform analysis. That is, rather than univariate analysis using a single variable, multivariate analysis which considers interaction of several variables is performed.

However, like the result of the related art, the multivariate analysis is not performed in a state where the effect of the survival rate on the MLD value is meaningless. This is because it is determined that it is meaningless in the univariate analysis.

However, when the continuous variable is appropriately transformed using a technique which adjusts the confounder for the continuous variable MLD of the present disclosure, the effect on the survival rate may be identified through the transformed continuous variable.

First, a process of finding a confounder which influences the MLD of the patient was performed. The scatter diagram illustrated in FIG. 7 schematically shows whether the MLD varies depending on each clinical variable. It is visually confirmed that the MLDs are different depending on variables as illustrated in C, D, and G. However, the difference is not visually verified, but the average of the MLD is compared for every variable to confirm whether the difference is statistically significant. As a result, only the clinical values whose p-value was smaller than 0.1 were considered as confounders which influenced the MLD.

The combinations of variables were created and C, D, G, H, J, L determined as confounders for the MLD were divided into subgroups having a value of each combination. Further, MLDs were transformed into new relative MLDs with "0" as a representative value of the MLD for every subgroup. In this case, the new MLD value is referred to as a new MLD. 96 (C(2)×D(3)×G(2)×H(2)×J(2)×L (2)) subgroups were generated. However, in each subgroup, when there was no person corresponding to a subgroup or one person corresponded to a subgroup, the subgroups were excluded and subgroups having two or more persons were included. Therefore, as illustrated in FIG. 9, new MLDs were generated using 38 subgroups.

A result of analyzing the effect on the survival rate using the new MLD generated as described above using the Cox-proportional Hazard model again is as follows:

Hazard Ratio: 1.075

Confidence interval (95% confidence interval of hazard ratio): 1.005-1.150

P-value (probability): 0.036

As a result of the present disclosure, it is understood that whenever the new MLD increases by 1 Gy, the survival rate has a bad effect of 1.075 times. P-value is 0.036, which is smaller than a normal significance level of 0.05, so that a significant result was deduced.

Therefore, as the exposure dose of the lung is increased, a result that the survival rate was adversely influenced was deduced. All the patients included in this study have MLD of 25 Gy or lower and it was determined that the survival rate is not influenced at this level. However, it was confirmed that even a low lung exposure dose may adversely influence the survival rate, through the analysis. This result suggests that when the radiation exposure amount of the lung is maintained as low as possible, the improvement of the survival rate may be maximized.

The exemplary embodiments of the present disclosure may be implemented as a program command which may be executed by various computers to be recorded in a computer-readable medium. The computer-readable medium may include solely a program command, a data file, and a data structure or a combination thereof. The program commands recorded in the medium may be specifically designed or constructed for the present invention or known to those skilled in the art of computer software to be used. Examples of the computer-readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program command such as a ROM, a RAM, and a flash memory. Examples of the program command include not only a machine language code which is created by a compiler but also a high-level language code which may be executed by a computer using an interpreter. The hardware device may operate as one or more software modules in order to perform the operation of the exemplary embodiments of the present disclosure and vice versa.

For now, the present invention has been described with reference to the exemplary embodiments. It is understood to those skilled in the art that the present invention may be implemented as a modified form without departing from an essential characteristic of the present invention. Therefore, the disclosed exemplary embodiments may be considered by way of illustration rather than limitation. The scope of the present invention is presented not in the above description but in the claims and it may be interpreted that all differences within an equivalent range thereto may be included in the present invention.

What is claimed is:

1. A treatment adjustment method by using adjusted continuous variables, comprising:
   analyzing, using a univariate analysis, a set of analysis data collected from a treatment wherein the set of analysis data comprises a continuous variable, a dependent variable, and a set of clinical variables, to determine a first correlation between the continuous variable and the dependent variable;
   determining one or more confounders from the set of analysis data based on an absence of the first correlation in the set of analysis data unveiled under the univariate analysis;
   classifying the set of analysis data into a plurality of subgroups having a same combination of the one or more confounders;
   generating a new continuous variable for each subgroup of the plurality of subgroups based on a representative value of a continuous variable distribution in each subgroup of the plurality of subgroups;
   analyzing a second correlation between the new continuous variable and the dependent variable for each subgroup of the plurality of subgroups; and
   adjusting the treatment based on a predetermined probability condition presented in the second correlation and affirming that the treatment needs no adjustment with regard to the new continuous variable based on an absence of the predetermined probability condition in the second correlation, and
   wherein the determining comprises:
     transforming a set of continuous variables included in the set of clinical variables into a set of categorical variables in the set of analysis data;
     calculating significance probabilities (p-values) by comparing the set of clinical variables with a mean of the continuous variable; and
     for each clinical variable in the set of clinical variables, determining the clinical variable having a significance probability which is smaller than a predetermined setting value, as a confounder,
   wherein the adjusting the treatment comprises:
     identifying, based on the second correlation, a treatment limit, under which, the treatment produces intended treatment effects and predetermined side effects; and
     applying the identified treatment limit, as a cap to be not exceeded during the treatment, in the treatment to increase a survival rate of a patient under the treatment.

2. The treatment adjustment method of claim 1, wherein the generating of the new continuous variable comprises:
   setting a representative value of the continuous variable distribution for each subgroup of the plurality of subgroups to be a "real number"; and
   transforming the continuous variable of each subgroup of the plurality of subgroups into a relative value with respect to the "real number".

3. A treatment adjustment method by analyzing a correlation between an adjusted continuous variable and a specific dependent variable of data to be analyzed, the method comprising:
   extracting information on a continuous variable, a dependent variable, and a set of clinical variables from a set of analysis data collected from a treatment;

determining one or more confounders from the set of clinical variables;

transforming the continuous variable into a new continuous variable using the one or more confounders;

analyzing the correlation between the new continuous variable and the dependent variable; and adjusting the treatment based on a predetermined probability condition presented in the correlation and affirming that the treatment needs no adjustment with regard to the new continuous variable based on an absence of the predetermined probability condition in the correlation, wherein the determining comprises:
 transforming a set of continuous variables included in the set of clinical variables into a set of categorical variables in the analysis data;
 calculating significance probabilities (p-values) by comparing the set of clinical variables with a mean of the continuous variable; and
 for each clinical variable in the set of clinical variables, determining the clinical variable having a significance probability which is smaller than a predetermined setting value, as a confounder, wherein the adjusting the treatment comprises:
 identifying, based on the second correlation, a treatment limit, under which, the treatment produces intended treatment effects and predetermined side effects; and
 applying the identified treatment limit, as a cap to be not exceeded during the treatment, in the treatment to increase a survival rate of a patient under the treatment.

4. The treatment adjustment method of claim 3, wherein the transforming into the new continuous variable comprises:

classifying the set of analysis data into a plurality of subgroups having a same combination of the one or more confounders;

setting a representative value of a continuous variable distribution for each subgroup of the plurality of subgroups to be a "real number"; and transforming the continuous variable of each subgroup of the plurality of subgroups into a relative value with respect to the"real number".

5. A treatment adjustment apparatus using correlation analysis and adjustment of a continuous variable, comprising:

one or more processors, one or more computer-readable non-transitory memories and one or more computer-readable, tangible and non-transitory storage devices;

an adjusting unit, in a form of one or more program modules, stored on at least one of the one or more computer-readable, tangible and non-transitory storage devices for execution by at least one of the one or more processors via one of the one or more computer-readable non-transitory memories, to determine one or more confounders from a set of data collected from a treatment and to be analyzed, and transform a continuous variable of the set of data into a new continuous variable using the one or more confounders; and a correlation analyzing unit, in a form of one or more program modules, stored on at least one of the one or more computer-readable, tangible and non-transitory storage devices for execution by at least one of the one or more processors via one of the one or more computer-readable non-transitory memories, to analyze a correlation between the new continuous variable and a dependent variable of the set of data, wherein the correlation, when a predetermined probability condition presented, is used to adjust the treatment based on the correlation, and wherein the correlation, when the predetermined probability condition absent, affirms that the treatment needs no adjustment with regard to the new continuous variable, wherein the adjusting unit:
 extracts a set of clinical variables from the set of data;
 for each of the set of clinical variables, calculates significance probabilities (p-values) by comparing each of the set of clinical variables with the continuous variable; and
 for each of the set of clinical variables, determines the clinical variable having a significance probability which is smaller than a predetermined setting value as a confounder, wherein the correlation analyzing unit, when is used to adjust the treatment based on the predetermined probability condition presented in the correlation,
 identifies, based on the correlation, a treatment limit, under which, the treatment produces intended treatment effects and predetermined side effects; and
 applies the identified treatment limit, as a cap not to be exceeded during the treatment, in the treatment to increase a survival rate of a patient under the treatment.

6. The treatment adjustment apparatus of claim 5, wherein the adjusting unit:

classifies the set of data into a plurality of subgroups having a same combination of the one or more confounders; and transforms the continuous variable of each subgroup of the plurality of subgroups into a relative value with respect to a "real number" with the "real number" as a representative value of a continuous variable distribution for each subgroup of the plurality of subgroups to generate a new continuous variable.

* * * * *